(12) United States Patent
Bates et al.

(10) Patent No.: US 7,611,738 B2
(45) Date of Patent: Nov. 3, 2009

(54) PROCESSES FOR EXTRACTING PHYTOCHEMICALS FROM POMEGRANATE SOLIDS AND COMPOSITIONS AND METHODS OF USE THEREOF

(75) Inventors: Byron Bates, Bakersfield, CA (US); Erich A. Fritz, Westlake Village, CA (US); Yair Steve Henig, Beverly Hills, CA (US); Harley R. Liker, Beverly Hills, CA (US)

(73) Assignee: POM Wonderful, LLC, Los Angeles, CA (US)

( * ) Notice: Subject to any disclaimer, the term of this patent is extended or adjusted under 35 U.S.C. 154(b) by 298 days.

(21) Appl. No.: 11/137,248

(22) Filed: May 24, 2005

(65) Prior Publication Data

US 2006/0269629 A1    Nov. 30, 2006

(51) Int. Cl.
*A61K 36/00* (2006.01)
(52) U.S. Cl. .................... 424/769; 424/725; 424/777
(58) Field of Classification Search ........................ None
See application file for complete search history.

(56) References Cited

U.S. PATENT DOCUMENTS

| | | | |
|---|---|---|---|
| 5,840,308 A | 11/1998 | Jassim et al. | |
| 5,891,440 A | 4/1999 | Lansky | |
| 5,902,616 A * | 5/1999 | Hinnergardt et al. | 426/52 |
| 5,989,557 A | 11/1999 | Bombardelli et al. | |
| 6,033,692 A | 3/2000 | Chukwu | |
| 6,060,063 A | 5/2000 | Lansky et al. | |
| 6,312,753 B1 | 11/2001 | Kealey et al. | |
| 6,361,807 B1 | 3/2002 | Aviram et al. | |
| 6,375,993 B1 | 4/2002 | Aviram et al. | |
| 6,387,370 B1 | 5/2002 | Yegorova | |
| 6,387,418 B1 | 5/2002 | Aviram et al. | |
| 6,544,581 B1 | 4/2003 | Shrikhande et al. | |
| 6,641,850 B1 | 11/2003 | Aviram et al. | |
| 6,642,277 B1 | 11/2003 | Howard et al. | |
| 6,800,292 B1 | 10/2004 | Murad | |
| 6,855,352 B2 | 2/2005 | Shoji | |
| 2002/0012710 A1 | 1/2002 | Lansky | |
| 2002/0197341 A1 | 12/2002 | Lansky | |
| 2003/0134006 A1 | 7/2003 | Chukwu | |
| 2004/0009262 A1 | 1/2004 | Chukwu | |
| 2004/0126470 A1 | 7/2004 | Harpaz | |
| 2005/0118312 A1 | 6/2005 | Lansky | |

FOREIGN PATENT DOCUMENTS

WO    WO 0137848          5/2001
WO    WO 02/094303 A1    11/2002

OTHER PUBLICATIONS

DW ACC 2003-103614, Dec. 2002, Derwent or WO, Lansky.*
Pantuck, et al., "Pomegranet Juice May Slow Prostate Cancer Growth," American Urological Association Annual Meeting, The Journal of Urology (Texas, US), vol. 173 (No. 4), p. 1057-1439, (Apr. 24, 2005).
Albrecht, Martin et al., "Pomegranate Extracts Potently Suppress Proliferation, Xenograft Growth, and Invasion of Human Prostate Cancer Cells," J Med Food 7 (3) 2004, 274-283.

* cited by examiner

*Primary Examiner*—Christopher R Tate
*Assistant Examiner*—Randall Winston
(74) *Attorney, Agent, or Firm*—Dalina Law Group P.C.

(57) ABSTRACT

Processes for producing an extract containing phytochemicals from pomegranates are disclosed. The processes generally comprise providing pomegranate solids, such as the pericarp, inner membrane and seeds; creating a mixture comprising the pomegranate solids in an aqueous solution; adding enzymes to the mixture in an amount sufficient to at least partially degrade the pomegranate solids; heating the mixture to a temperature that permits the maximum rate of catalysis of the enzyme; maintaining the temperature of the heated mixture for a time sufficient to allow at least partial degradation of the pomegranate solids; and removing residual insoluble solid materials from the mixture. Compositions containing the extract may be used as a food product, beverage, pharmaceutical preparations, nutritional supplements, vitamin supplements, food additives, and food supplements. The composition may also be used for preventing or ameliorating disease conditions by administering an effective amount of the composition to a subject in need thereof.

10 Claims, No Drawings

PROCESSES FOR EXTRACTING PHYTOCHEMICALS FROM POMEGRANATE SOLIDS AND COMPOSITIONS AND METHODS OF USE THEREOF

FIELD OF THE INVENTION

The present invention relates generally to pomegranate extracts, and more particularly, to methods for obtaining and using extracts from pomegranate solids and compositions comprising pomegranate extracts.

BACKGROUND OF THE INVENTION

It is well-known that fruits and vegetables are an essential part of a healthy diet. Chief, among the reasons, is that fruits and vegetables are rich sources of important phytochemicals, which provide essential nutrients and enhance the body's ability to prevent and fight disease. There is a multitude of phytochemicals, in unique combinations, in different fruits and vegetables, and each functions differently in the body: as anti-oxidants, as anti-allergenic, as anti-carcinogenic, as anti-inflammatory, as anti-viral, and/or anti-proliferative.

The pomegranate has recently been acclaimed for its health benefits and for its disease-fighting antioxidant potential. Antioxidants are important because they are believed to protect the body against free radicals, the harmful molecules that can cause heart disease, premature aging, Alzheimer's disease, blindness, and a variety of cancers.

Studies have shown that pomegranate juice has more polyphenol antioxidants than any other drink, such as red wine, green tea, blueberry juice, cranberry juice and orange juice. Currently, the two common ways of consuming pomegranates are by eating the fleshy arils of the pomegranate and by drinking the juice obtained from the arils.

There are many kinds of antioxidants, some produced by the body and others derived from the foods we eat. When the body's natural antioxidant defenses are lowered, or greater amounts of free radicals are being produced, the body becomes more dependent upon food sources of antioxidants.

BRIEF SUMMARY OF THE PREFERRED EMBODIMENTS

Methods are provided for producing an extract containing phytochemicals from pomegranate solids. The pomegranate solids are any one or more of the group consisting of the pericarp, inner membrane and seeds. The extract produced differs from commercially-available pomegranate juice in that the extract is substantially derived from the pomegranate solids, whereas pomegranate juice is substantially derived from the sweet, fleshy arils.

In one preferred embodiment, the method includes the following steps. Any one or a combination of the pericarp, inner membrane and seeds are selected and a mixture is formed comprising the pomegranate solids and an aqueous solution. The mixture is then heated to about 60° F. to 210° F., preferably of about 85° F. to 185° F. and optimally of about 110° F. to 160° F. Enzymes are added to the mixture in an amount sufficient to at least partially degrade the pomegranate solids and liberate phytochemicals from the plant tissues and/or cells. Once liberated, the phytochemicals may react and/or polymerize to create new phytochemical compounds or reaction products. The residual insoluble solid materials are removed from the mixture to provide an extract containing phytochemicals.

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein.

In a further preferred embodiment, food products and beverages are provided comprising the extract containing phytochemicals from a pomegranate.

In yet a further preferred embodiment, compositions comprising the extract containing phytochemicals from a pomegranate are provided. Such compositions may be in form of tablets, suspensions, implants, solutions, emulsions, capsules, powders, syrups, liquid compositions, ointments, lotions, creams, pastes, and gels. Such compositions may also be in form of pharmaceutical preparations, nutritional supplements, vitamin supplements, food additives, and food supplements.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract.

In another preferred embodiment, methods are provided for preventing or ameliorating disease conditions in a subject by administering to the subject an effective amount of the composition suitable for use as a pharmaceutical or nutritional preparation. Such disease conditions include polyphenol-mediated diseases and cancer. Examples of polyphenol-mediated diseases include circulatory disorders such as hypertension and coronary artery disease, erectile dysfunction, lung disorders such as asthma, cancers of various types, inflammatory conditions, certain liver conditions, diabetes, mood disorders, eye disorders such as cataracts, weak eyesight due to aging, macular degeneration, and other age-related disorders, such as Alzheimer's disease and dementia.

In yet another preferred embodiment, methods are provided for modulating the growth and progression of cancerous cells, the methods comprising selecting a subject having cancerous cell growth and administering to the subject an effective amount of the composition containing the extract.

In yet a further preferred embodiment, methods are provided for preventing or slowing increases in the Prostate Specific Antigen (PSA) levels in a subject having prostate cancer. The method comprises selecting a subject having prostate cancer and administering to the subject an effective amount of the composition containing the extract.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications and equivalents thereof.

DETAILED DESCRIPTION OF THE PREFERRED EMBODIMENTS

As used herein, the term "phytochemicals" refers collectively to compounds which are naturally-occurring in the pomegranate and to reaction products and metabolites of these compounds, which are considered to have a beneficial effect on the human health. Examples of such phytochemicals include, but are not limited to polyphenols, estrogens and phytoestrogens.

As used herein, the term "polyphenols" refers generally to a family of naturally-occurring compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic acid and gallic acid. Polyphenols are a group of compounds, characterized by the presence of more than one phenolic group. Polyphenols include tannins (e.g., ellagitannins and gallotannins), flavonoids (e.g., anthocyanins and isoflavones) and stilbenes (e.g., resveratrol).

As used herein, the term "pomegranate juice" refers to the juice that is substantially obtained from the arils of the pomegranate.

As used herein, the term "pomegranate solids" refers to any one or a combination of the pericarp, the inner membrane and seeds of a pomegranate.

It has been surprisingly discovered that extracts obtained from the pomegranate solids, in accordance with the methods disclosed herein, have a substantially higher total polyphenol content than is found in the juice from the pomegranate arils. This is particularly true with respect to the higher molecular weight polyphenols and, in particular, punicalagin.

Punicalagin is a powerful antioxidant, protecting cardiovascular function and accurate cellular replication. Thus, punicalagin is responsible, in part, for the high antioxidant activity of the extract. While the antioxidant and other beneficial health effects of the extract are due to the presence of polyphenols, the presence of other phytochemical compounds in the extract, or the synergistic effect of these phytochemicals, may also be responsible for the anti-oxidant and other beneficial health effects of the extract.

In addition to punicalagin, other high molecular weight polyphenols have been characterized in the extract of pomegranate solids. These high molecular weight polyphenols include ellagitannin and other hydrolysable tannins, such as punicacortein A, punicalin, pedunculagin, and gallotanin dimers and trimers.

Moreover, a large number of anthocyanins have been characterized in the extract of the pomegranate solids. Examples of the anthocyanins include pelargonidin 3-glucoside, cyaniding 3-glucoside, delphinidin 3-glucoside, pelargonidin 3,5-diglucoside, cyaniding 3,5-diglucoside, and delphinidin 3,5-diglucoside. Although these anthocyanins have been characterized in both the pomegranate juice and the extract, these lower molecular weight polyphenols comprise a higher proportion of the total polyphenol content in pomegranate juice (approximately 50%) than in the extract.

Accordingly, methods are provided for producing an extract containing phytochemicals from pomegranate solids. The extract produced from the methods disclosed herein differ from the commercially-available pomegranate juice in that the extract is substantially derived from the pomegranate solids, whereas pomegranate juice is substantially derived from the sweet, fleshy arils that surround the pomegranate seed. The extract is characterized as containing polyphenols and, particularly, high molecular weight polyphenols, such as punicalagin.

In one preferred embodiment, the method comprises providing any one or a combination of pomegranate solids selected from the group consisting of the pericarp, inner membrane and seeds and creating a mixture comprising the pomegranate solids in an aqueous solution. In a preferred embodiment, the mixture of the pomegranate solids is created by adding water in an amount that is about 20-80% w/v, and more preferably about 50% w/v, of the pomegranate solids. The mixture is preferably crushed or milled to create a rough grind of pomegranate solids dispersed in the aqueous solution.

The mixture is then heated to a temperature of about 60° F. to 210° F., preferably of about 85° F. to 185° F. and optimally of about 110° F. to 160° F. The temperature to which the mixture is heated depends upon the selection of enzymes, or combination of enzymes, that is added to the mixture. Preferably, the mixture is heated to a temperature that permits the maximum catalysis of the enzyme or combination of enzymes.

Alternatively, enzymes may be added before the mixture is heated. Thus, the order of the steps of heating the mixture and adding the enzymes is not critical, so long as the mixture is heated to a temperature that permits the enzymes to at least partially degrade the pomegranate solids and liberate phytochemicals from the plant tissues and/or cells. Once liberated, the phytochemicals may react and/or polymerize to create new phytochemical compounds or reaction products.

Enzymes suitable for use in accordance with this embodiment include those which are capable of at least partially degrading the plant tissue or cells to liberate the phytochemicals from the pomegranate solids. Such enzymes include any one or a combination of pectinase, cellulase, hemicellulase, amylase, arabanase, and other hydrolyzing enzymes, to name a few. The enzymes added to the mixture may be naturally-occurring or synthetic. They may be derived from any one or a combination of sources, such as animal, plant, fungal, and bacterial sources. The amount of the enzyme or combination of enzymes added to the mixture depends on the temperature of the mixture and the amount of pomegranate solids present in the mixture.

After enzymes are added, the mixture is maintained at a temperature for a time sufficient to allow at least partial degradation of the pomegranate solids. The temperature and length of time required depends on the type of enzymes added to the mixture, the rate of enzyme catalysis and the amount of the pomegranate solids contained in the mixture.

Thus, in one preferred embodiment, a combination of pectinase, cellulase and hemicellulase enzymes are added to the mixture, which is heated to a temperature of about 60° F. to 210° F., preferably about 110° F. to 160° F., and optimally of about 120° F. The mixture is maintained at these temperature, preferably with agitation or stirring, for about 45-195 minutes, preferably for about 45-75 minutes, and optimally for about 60 minutes.

After the enzymes have at least partially degraded the pomegranate solids, the residual insoluble solid materials are removed from the mixture. Optionally, a clarification agent, such as bentonite, may be added before the step of removing the residual insoluble materials from the mixture. The removal of residual insoluble materials from the mixture may be accomplished by filtration, centrifugation, chromatographic techniques, and other techniques. Filtration techniques suitable for the practice of the methods disclosed herein include micro-filtration at a molecular weight cut-off of at least 1,000 Da, preferably of about 4,500 Da, and optimally of about 5,500 Da.

The resulting liquid extract may be concentrated in an evaporator under vacuum to about 50-90 Brix (Bx), preferably to about 60-80 Bx, and optimally to about 70 Bx, and pasteurized at a temperature and for a length of time sufficient to kill microorganisms that could cause disease, spoilage or undesired fermentation. In one preferred embodiment, the extract may be pasteurized at a temperature of about 140° F.-280° F., preferably of about 195° F.-240° F., and optimally of about 205° F. The pasteurization may also denature the remaining enzymes that were added to the mixture.

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein. In a further preferred embodiment, extracts containing phytochemicals, polyphenols, punicalagin, punicalin, ellagic acid, and metabolite thereof are provided.

In yet another preferred embodiment, food products and beverages are provided comprising the extract containing phytochemicals from a pomegranate. For example, due to the significantly higher total polyphenol content in the extract, an 8 oz sports beverage containing 0.33 oz of the extract may be formulated to deliver the same total polyphenols as a 20 oz single-strength pomegranate juice. The polyphenol content of pomegranate juice is approximately about 1 to 2.25 mg/mL and the amount of polyphenols present in 20 oz of juice is approximately 567 to 1,256 mg. In contrast, the extract may contain a polyphenol content of about 60 to 120 mg/mL, depending on the method employed. Thus only 0.33 oz of the 70 Bx extract would be needed to provide the equivalent amount of polyphenols in 20 oz of the juice.

In a further preferred embodiment, compositions comprising the extract containing phytochemicals from a pomegranate are provided. The compositions may be formulated in the form of tablets, suspensions, implants, solutions, emulsions, capsules, powders, syrups, liquid compositions, ointments, lotions, creams, pastes, gels, and the like.

The compositions may also be prepared in forms suitable for use as pharmaceutical preparations, nutritional supplements, vitamin supplements, food supplements, and food additives. As such, the compositions may optionally include a suitable carrier or excipient.

Suitable carriers or excipients are inert ingredients and include, by way of example, fillers, e.g. sugars such as lactose, glucose or sucrose, sugar alcohols such as mannitol, sorbitol or xylitol, starch such as wheat, corn or potato starch, modified starch or sodium starch glycolate, lubricants such as talc, magnesium stearate, calcium stearate, colloidal silica or stearic acid, and binders such as polyvinylpyrrolidone, cellulose derivatives, carboxymethyl cellulose, hydroxylpropyl cellulose, hydroxypropylmethyl cellulose, methyl cellulose or gelatin. Conventional procedures for preparing such compositions in appropriate dosage forms of the extract may be utilized. Such compositions may be administered orally or parenterally employing liquid form preparations containing the extract.

The compositions may be administered orally, in appropriate dosage units of the extract in a pharmaceutically acceptable carrier or excipient. Thus, the compositions may be formulated into solid or liquid preparations, such as capsules, pills, tablets, powders, solutions, suspension, or emulsions and may be prepared according to methods known in the art for the manufacture of such compositions. The solid unit dosage forms may be in form of a hard or soft shelled gelatin capsule containing the extract and a suitable carrier or excipient.

The composition may also be administered parenterally as injectable dosages in a physiologically acceptable carrier. Parenteral administration may be subcutaneous, intravenous, intramuscular, or interperitoneally.

The effective amount of a composition is the amount or dosage unit of the extract sufficient to achieve the intended beneficial health results. Accordingly, the effective amount of the composition to be administered depends on considerations such as the dosage unit employed, the mode of administration, the period of treatment, the age, sex and weight of the person treated and the nature and extent of the condition treated. The effective amount can readily be determined based upon standard techniques known to evaluate whether the intended effect of the composition has been achieved, by standard toxicity tests and by standard pharmacological assays.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract, for example the lower molecular weight polyphenols (e.g., anthocyanins) which is present in greater quantities in the pomegranate juice and the higher molecular weight polyphenols (e.g., punicalagin, punicalin, ellagic acid glycosides, ellagic acid polyphenols, ellagitannin and other hydrolysable tannins, such as punicacortein A, punicalin, pedunculagin, and gallotanin dimmers and trimers).

In yet a further preferred embodiment, methods are provided for ameliorating disease conditions in a subject by administering to the subject an effective amount of the composition suitable for use as a pharmaceutical or nutritional preparation. Such disease conditions include polyphenol-mediated diseases and cancer.

Polyphenols and countless other phytochemicals in the extract are necessary for the various organs and tissues and for the proper functioning of the human body. Accordingly, many disease conditions may be prevented or ameliorated by the administration of polyphenols to patients with polyphenol-mediated diseases. These polyphenol-mediated diseases include circulatory disorders such as hypertension and coronary artery disease, erectile dysfunction, lung disorders such as asthma, cancers of various types, inflammatory conditions, certain liver conditions, diabetes, mood disorders, eye disorders such as cataracts, weak eyesight due to aging, macular degeneration, and other age-related disorders, such as Alzheimer's disease and dementia.

Thus, in one preferred embodiment, methods are provided for formulating a composition suitable for use as a pharmaceutical or nutritional preparation for improving the health of a subject comprising obtaining an extract containing phytochemicals from a pomegranate and admixing an effective amount of the extract with a suitable carrier or excipient.

In another preferred embodiment, methods are provided for treating a polyphenol-mediated condition in a subject comprising selecting a subject having a polyphenol-mediated condition and administering to the subject an effective amount of the composition comprising the extract.

In yet another preferred embodiment, methods are provided for modulating the growth and progression of cancerous cells, the methods comprising selecting a subject having cancerous cell growth and administering to the subject an effective amount of the composition containing the extract.

In yet a further embodiment, methods are provided for preventing or slowing increases in the Prostate Specific Antigen (PSA) levels in a subject having prostate cancer. The method comprises selecting a subject having prostate cancer and administering to the subject an effective amount of the composition containing the extract.

Prostate cancer is the most commonly detected cancer in men in the U.S., affecting approximately 1 out of every 6 men. It is the second leading cause of cancer death among men in the U.S. Laboratory testing can assist with screening, diagnosis, staging, prognosis, detection of residual or recurrent disease, and therapeutic monitoring. The primary test used for these purposes is a PSA test.

The PSA test was approved by the FDA in 1986 to help detect prostate cancer. A number of prostate problems can be identified by testing and monitoring the levels of PSA circulating in the bloodstream. The level of PSA in the bloodstream may be elevated by an process that leads to an increase in the number of cells making PSA or to a breakdown of the normal barriers in the prostate that prevent much PSA from getting into the bloodstream.

Increases in levels of PSA in the blood following treatment for localized prostate cancer with surgery or radiation often indicates the presence of residual cancer and the eventual development of metastatic cancer. Moreover, PSA doubling times are correlated with diagnostic tumor stage and grade The following examples further illustrate the embodiments disclosed herein. These examples are provided only for purpose of illustrating the preferred embodiments of the invention and do not limit the invention in any manner.

EXAMPLE 1

Production of Liquid Extract from Pomegranate Solids

The starting material for the production of the extract is the pomegranate solids, which generally comprise the pericarp, the inner membrane and seeds of the pomegranate. The pomegranate solids were obtained and collected after the primary juice from the arils had been substantially expelled or otherwise removed from the pomegranate by pressing, crushing, or other methods known to the art for extracting pomegranate juice.

The pomegranate solids were then transferred to three Reitz Mills with ⅜-inch screens. The material was milled to a fine puree and heated to approximately 125° F. This step, coupled with the following enzyme addition, assisted in breaking down the colloidal structure of the remaining pomegranate solids, thereby releasing the remaining soluble solids.

The mixture was heated to a temperature of about 125° F. for two hours. Three enzymes were added to the mixture: pectinase (Rohapect® DA6L), cellulase/pectinase (Rohapect® CL), and hemi-cellulase/pectinase (Rohapect® B1L). These enzymes were used to liberate the remaining pomegranate soluble solids, such as sugars, minerals, anthocyanins, and remaining polyphenols.

The mixture was then pumped from the extraction plant to the primary processing plant where it was held in the mash treatment tanks for approximately one hour. After one hour, 50-100 pounds of bentonite in a 125 galloon water slurry, per 8,000 gallons of the mixture, was added for protein removal. The treated mixture was then passed through a Westphalia 755 Decanter for removal of solids. The residual insoluble material was discharged as waste.

The remaining liquid extract was processed in a Schmidt evaporator. In this step, the extract was stripped and rectified. In addition, the liquid extract was pre-concentrated and then pasteurized to 205° F. for 45 seconds. The liquid extract then exited the evaporator and was filtered on Koch Micro-Filtration membranes at a 4,500 Da molecular weight cut-off for liquid extract soluble solids.

The liquid extract then re-entered the evaporator for final concentration. Initial heat on this step was about 185-195° F. At about 70 Bx, the liquid extract was cooled to less than about 45° F. and pumped to the concentrate batching room where it was blended and standardized.

EXAMPLE 2

Comparison of Polyphenol Content in Extracts of Pomegranate Solids and in Pomegranate Juice The concentrations of punicalagin, punicalin, ellagic acid glycosides, and ellagic acid polyphenols in the pomegranate juice and the pomegranate extract were analyzed and compared in a University study.

All samples (50 mL injection volume) were filtered (0.22 mm) and analyzed on a Novapak (Waters Corp.) C-18 column, 150×3.9 mm i.d., 5 mm. The mobile phase, solvent A (2% $CH_3COOH/H_2O$) and solvent B (2% aqueous $CH_3COOH/CH_3OH$) was used under linear gradient conditions starting with 99% solvent A in solvent B to 40% solvent A in solvent B over 40 minutes, hold time, 5 minutes with a flow rate of 1 mL/min. All compounds were detected at 254 nm, and at 378 nm (punicalagins) and 366 (ellagic acid) for quantification.

Table 1 shows a side-by-side comparison of the concentration of the polyphenols punicalagins, punicalin, ellagic acid glycosides, and ellagic acid in the pomegranate extract and the pomegranate juice.

TABLE 1

| Compound Name | Pomegranate Extract Concentration (mg/ml) | Pomegranate Juice Concentration (mg/ml) |
| --- | --- | --- |
| Punicalagin (β-isomer) | 4.79 | 0.02 |
| Punicalagin (α-isomer) | 21.80 | 0.15 |
| Punicalin | 3.62 | NA |
| Ellagic Acid Glycosides | 19.65 | 0.33 |
| Ellagic Acid | 18 | 0.74 |
| Total: | 67.86 | 1.24 |

Although other polyphenols are present in both the pomegranate extract and juice, and this example highlights the unexpected and surprising results in that significantly higher concentrations of polyphenols, particularly of punicalagin, are present in the pomegranate extract than in the pomegranate juice. Table 1 shows a total punicalagin (for both α- and β-isomers) concentration for the pomegranate extract that is over 26-fold greater than for the pomegranate juice.

EXAMPLE 3

Effects of Pomegranate Juice in Men with Rising PSA Following Surgery or Radiation for Prostrate Cancer The positive and significant beneficial effects of pomegranate juice on Prostate Specific Antigen (PSA) parameters have been demonstrated in a clinical trial in patients with recurrent prostrate cancer, coupled with corresponding laboratory effects on prostrate cancer in in vitro cell growth and apoptosis.

To determine the clinical effects of pomegranate juice on patients with prostate cancer, a clinical trial was performed. A two-year, single center, phase II, Simon two stage clinical trial for men with rising PSA after surgery or radiotherapy was designed based on a 20% response rate, an alpha of 5%, and 90% power. Eligible patients had a detectable PSA greater than 0.2 ng/ml and less than 5 ng/ml, and a Gleason score of 7 or less. Serial PSA measurements determined a baseline PSA doubling time.

Patients were treated with 8 oz of pomegranate juice by mouth daily (Wonderful variety, equivalent to 1.5 mmol of total polyphenols per day) until disease progression. Clinical endpoints included safety, effect on serum PSA, and exploratory laboratory studies. Patients were followed in 3-month intervals for serum PSA, and blood and urine were collected for laboratory studies.

The study was fully accrued to 48 participants in two stages after efficacy criteria were met. There were no serious adverse events reported and the treatment was well tolerated. No patients developed metastatic disease on study. Mean PSA doubling time significantly increased with treatment, from a mean of 14 to 26 months (p<0.048). The slope of the mean log PSA decreased from 0.08 to 0.04 on treatment (p<0.019). In vitro assays using pre- and post-treatment patient serum on the growth of LNCaP showed decreased cell proliferation and increased apoptosis (p<0.07). Pomegranate polyphenols were detected in the urine of all participants by liquid chromatography mass spectrometry (LC-MS).

EXAMPLE 4

Preventing or Slowing Increases in the PSA Levels of Patients With Prostate Cancer While both pomegranate juice and pomegranate solid extract contain various types of the anti-oxidant polyphenols, pomegranate solid extract contains a higher total polyphenol content than the pomegranate juice. Accordingly, to the extent that the administration of 8 oz of pomegranate juice to patients with prostate cancer has been demonstrated to increase the PSA doubling time in patients with prostate cancer, the administration of pomegranate solid extract also achieves at least the same, and preferably an improved, effect.

Accordingly, methods and compositions are provided for preventing or slowing increases in the Prostate Specific Antigen (PSA) levels in a patient. The methods comprise selecting a subject having prostate cancer and administering to the subject an effective amount of a composition containing the extract containing phytochemicals from a pomegranate solid.

In preferred one embodiment, the composition may be in form of a liquid comprising the extract and pomegranate juice. The total polyphenol content provided by the liquid may be varied by the changing the amount of the pomegranate extract and pomegranate juice contained in the liquid. Table 2 provides examples of the formulations of the liquid composition and the total polyphenol content in the formulations relative to the total polyphenol content in standard pomegranate juice.

TABLE 2

| Extract/Pomegranate Juice Liquid Composition | Pomegranate Extract (oz) | Pomegranate Juice (oz) |
| --- | --- | --- |
| Formulation 1 2× polyphenol content | 0.13 | 8 |
| Formulation 2 3× polyphenol content | 0.26 | 8 |
| Formulation 3 4× polyphenol content | 0.39 | 8 |
| Formulation 4 5× polyphenol content | 0.52 | 8 |

For purposes of this embodiment, the effective amount of the extract that is administered to the patient is at least 0.13 oz (or an equivalent unit or measurement) of the extract administered daily, whether the extract is provided alone or in a composition. Because the administration of 8 oz of pomegranate juice was found to be effective in slowing the rising PSA levels in patients with prostate cancer, the administration of at least 0.13 oz of the pomegranate solid extract is believed to achieve the same, if not improved, results. The dosage of the extract may be increased by administering a greater dosage or increasing the frequency at which the extract is administered.

In addition to the liquid compositions containing the extract, the extract may also be administered in a solid form, such as pharmaceutical or nutritional preparation that comprise the extract and a pharmaceutically acceptable carrier or excipient.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims

The invention claimed is:

1. A method of modulating growth and progression of cancerous cells, the method comprising:
   selecting a subject having cancerous cell growth;
   administering to said subject a composition comprising an effective amount of a pomegranate extract, whereby said pomegranate extract is produced by a process comprising:
      providing one or more pomegranate solids selected from the group consisting of a pericarp, inner membrane and seeds;
      creating a mixture comprising said one or more pomegranate solids in an aqueous solution;
      adding hydrolyzing enzymes to said mixture in an amount sufficient to at least partially degrade said one or more pomegranate solids;
      heating said mixture to a temperature that permits enzyme catalysis of said pomegranate solids;
      maintaining said mixture at a temperature and time sufficient to allow at least partial degradation of the pomegranate solids;
      and removing residual insoluble solid materials from said mixture to provide an extract, wherein said extract contains polyphenols.

2. A method of modulating growth and progression of cancerous cells comprising:

selecting a subject having cancerous cell growth;
administering to said subject a composition comprising an effective amount of a pomegranate extract and pomegranate juice, whereby said pomegranate extract is produced by a process comprising:
    providing one or more pomegranate solids;
    creating a mixture comprising said one or more pomegranate solids in an aqueous solution;
    adding hydrolyzing enzymes to said mixture in an amount sufficient to at least partially degrade said one or more pomegranate solids;
    heating said mixture to a temperature that permits enzyme catalysis of said pomegranate solids;
    maintaining said mixture at a temperature and time sufficient to allow at least partial degradation of said one or more pomegranate solids;
    and removing residual insoluble solid materials from said mixture to provide an extract, wherein said extract contains polyphenols.

3. The method of claim 2 wherein said pomegranate solid is selected from the group consisting of pericarp, inner membrane and seeds from a pomegranate fruit.

4. The method of claim 3 wherein said pomegranate solid comprises the remainder of a whole pomegranate fruit following extraction of substantially all liquid from arils of said whole pomegranate fruit.

5. A method of increasing Prostate Specific Antigen doubling time in a subject having prostate cancer comprising:
    selecting a subject having prostate cancer;
    administering to said subject a composition comprising an effective amount of a pomegranate extract, whereby said pomegranate extract is produced by a process comprising:
    obtaining one or more pomegranate solids;
    creating a mixture comprising said one or more pomegranate solids in an aqueous solution;
    adding hydrolyzing enzymes to said mixture in an amount sufficient to at least partially degrade said one or more pomegranate solids;
    heating said mixture to a temperature that permits enzyme catalysis of said one or more pomegranate solids;
    maintaining said mixture at a temperature and time sufficient to allow at least partial degradation of said one or more pomegranate solids;
    and removing residual insoluble solid materials from said mixture to provide an extract, wherein said extract contains polyphenols.

6. The method of claim 5 wherein said pomegranate solid is selected from the group consisting of pericarp, inner membrane and seeds from a pomegranate fruit.

7. The method of claim 5 wherein said pomegranate solid comprises the remainder of a whole pomegranate fruit following extraction of substantially all liquid from arils of said whole pomegranate fruit.

8. A method of increasing Prostate Specific Antigen doubling time in a subject having prostate cancer, the method comprising:
    selecting a subject having prostate cancer;
    administering to said subject a composition comprising an effective amount of a pomegranate extract and pomegranate juice, whereby said pomegranate extract is produced by a process comprising of
    providing one or more pomegranate solids;
    creating a mixture comprising said one or more pomegranate solids in an aqueous solution;
    adding hydrolyzing enzymes to said mixture in an amount sufficient to at least partially degrade said pomegranate solids;
    heating said mixture to a temperature that permits enzyme catalysis of said one or more pomegranate solids;
    maintaining said mixture at a temperature and time sufficient to allow at least partial degradation of said one or more pomegranate solids;
    and removing residual insoluble solid materials from said mixture to provide an extract, wherein said extract contains polyphenols.

9. The method of claim 8 wherein said pomegranate solid is selected from the group consisting of pericarp, inner membrane and seeds from a pomegranate fruit.

10. The method of claim 8 wherein said pomegranate solid comprises the remainder of a whole pomegranate fruit following extraction of substantially all liquid from arils of said whole pomegranate fruit.

* * * * *